United States Patent [19]

Mikkelsen

[11] Plant 5,153

[45] Dec. 6, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,076

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Cosmos and characterized by its intense mauve flower color; long, narrow variegated foliage; self-branching, thin stems and procumbent growth, making the cultivar ideal for hanging baskets; early and continuous flowering, with flower intensity and variegation being most pronounced in high light conditions.

1 Drawing Figure

The present invention relates to a new and distinctive cultivar of Impatiens plant, botanically known as Impatiens, and known by the cultivar name Cosmos. The new cultivar was developed by me through controlled breeding in Ashtabula, Ohio. The seed parent was 77-682-2 (Mikkelsen), and the pollen parent was 77-719-4 (Mikkelsen). Asexual reproduction of terminal or stem cuttings has shown that the unique features of this new impatiens are stabilized and are reproduced true to type in successive propagations.

The following characteristics distinguish Cosmos from both its parent varieties and other cultivated impatiens of this type known and used in the floriculture industry:

1. A thin stemmed, self-branching bushy plant with long narrow leaves when compared to Columbia or Corona, other new impatiens cultivars of applicant disclosed in pending applications.

2. Foliage is variegated in the basal and mid-vein areas, more so than in Columbia, Corona, or Gemini, with the latter also being disclosed in a pending application of applicant.

3. The flower color is an intense mauve similar to the color of the New Guinea Impatiens hybrid Rainbow (not patented), but the new cultivar is more floriferous and earlier flowering than Rainbow.

4. Self-branching, thin stems, and the procumbent growth characteristic of Cosmos are ideal qualities for hanging baskets. If Cosmos is planted into the ground, sufficient space must be given between plants to avoid overcrowding and soft growth.

5. Flowering is early and continuous, with medium small to medium sized flowers; most floriferous in full sunlight and long days.

6. Leaf variegation is quite dominant, giving a strong dilution to the green area.

7. Cosmos is a companion cultivar to Twinkles in growth habit, flowering habit, size and general appearance except for flower color. Twinkles is disclosed in a further pending application of applicant.

8. High light and ample nutrition are essential for greatest expression of flower color and leaf variegation.

The accompanying colored photograph taken in mid-September outdoors illustrates the overall appearance of Cosmos. The photo is a generally top perspective view of the plant and shows the colors as true as it is reasonably possible to obtain in a colored reproduction of this type.

The following is a detailed description of my new impatiens cultivar based on plants produced under commercial practices in Ashtabula, Ohio. The illustration shows a single specimen planted outside the first week of June from a 4" pot. By mid-September the plant measured nearly 60 cm. in diameter and 25 cm. high. Color references are made to The Royal Horticultural Society Colour Chart except where general terms of ordinary dictionary significance are used.

Parentage: Mikkelsen seedling 77-682-2 × Mikkelsen seedling 77-719-4.

Propagation:

(A) *Stem cuttings.*—Cutting 15 mm. long will develop to 4–5 cm. in 21–28 days.

(B) *Time to initiate roots.*—8–10 days at 23° C. summer.

*Time to initiate roots.*—12–14 days at 20° C. winter.

(C) *Rooting habit.*—Very fibrous, dendritic, abundant.

Plant description:

(A) *Form.*—A medium height flowering herb with red stems, medium internodes, self-branching, semi-loose type form.

(B) *Habit of growth.*—Free growing, self-branching, somewhat procumbent growth.

(C) *Foliage.*—Long, narrow, highly variegated, opposite, developing whorls as flowering develops.

(1) *Size.*—9–10 cm. long and 2 cm. wide.

(2) *Shape.*—Lanceolate, slightly concave when young, to terminal reflexing at maturity.

(3) *Texture.*—Upper surface rugose, under surface glabrous.

(4) *Margin.*—Entire.

(5) *Color.*—Young foliage, top side between 137B and 139B with strong variegation, under side lighter, 147C; mature foliage, top side same as young foliage; variegation is yellow/orange 16B.

(6) *Venation.*—Pinnate.

Flowering description:

(A) *Flowering.*—Early and continuous, with 5 or 6 buds in a whorl of leaves opening successively in 10 days, and each flower remaining for 8–10 days.

(B) *Natural flowering season.*—Indeterminate and continuous as long as plant develops new growth.

(C) *Flower buds.*—Ellipsoidal, flowers perfect, 5 cm. red spur originating from dominant sepal and having an open throat behind the ovary.

(D) *Flowers borne.*—Flowers are carried on longer than average pedicels, placing flowers well above the foliage of the whorl from which the flowers originate.

(E) *Quantity of flowers.*—Usually one flower per leaf in the whorl numbering 5–6 leaves.

(F) *Petals.*—(1) Shape: Top petal is dominant over 4 over-lapping heart-shaped symmetrical lower petals. (2) Color, Top side in summer when opening, between red purple 58B-C, with light pink ring around area of ovary, fading only slightly to red 55A; under side red purple 58C-D. (3) Number of petals: Five (5). (4) Size of flowers: 3.5 to 4 cm. in diameter.

(G) *Reproductive organs.*—(1) Stamens: Five (5) in number. a. Anther shape; Hooded; light pink in color. b. Pollen color: Cream. (2) Pistils: a. Stigma: Five (5) in number, segmented column-shaped, nearly colorless. b. Style: Colorless. c. Ovaries: Five (5) in number, celled; size 3 mm. before fertilized, green in color. Capsule is explosively dehiscent.

Disease resistance: New cultivar is somewhat susceptable to soft rot organisms during periods of cool wet weather outdoors in late summer and fall. To date there is no evidence of major insect or disease problems.

I claim:

1. A new and distinct cultivar of impatiens plant known by the cultivar name Cosmos, as described and illustrated, and particularly characterized by its intense mauve flower color; long, narrow variegated foliage; self-branching, thin stems and procumbent growth, making the cultivar ideal for hanging baskets; early and continous flowering, with flower intensity and variegation being most pronounced in high light conditions.

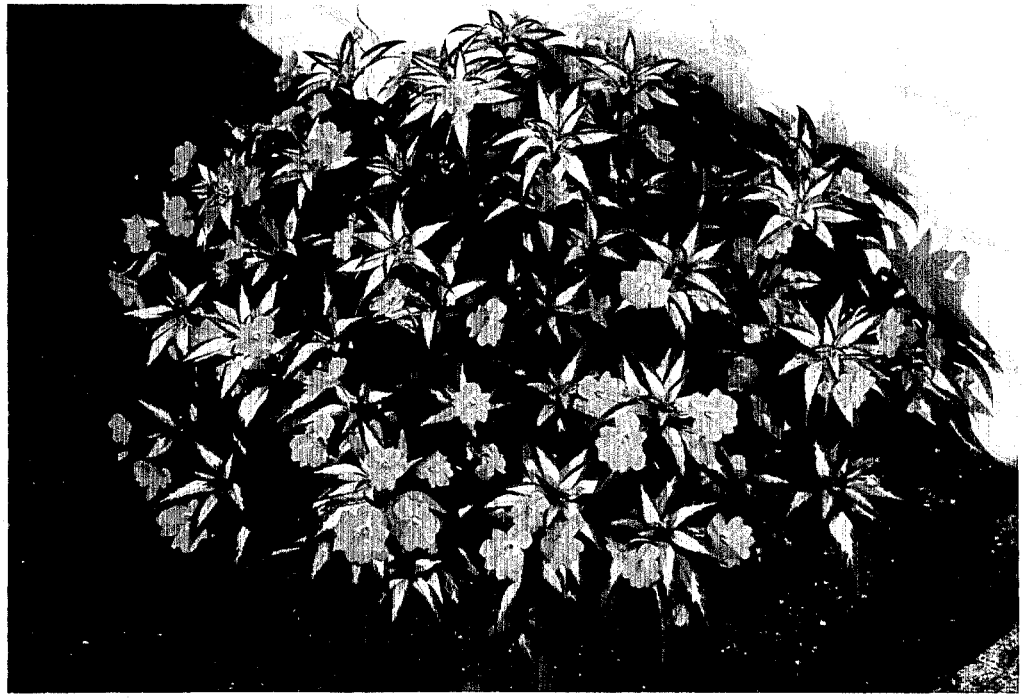

* * * * *